(12) United States Patent
Letort

(10) Patent No.: US 8,388,671 B2
(45) Date of Patent: Mar. 5, 2013

(54) METHODS FOR TREATMENT OF ANEURYSMAL TISSUE

(75) Inventor: Michel Letort, Prevessins (FR)

(73) Assignee: Medtronic Vascular, Inc., Santa Rosa, CA (US)

(*) Notice: Subject to any disclaimer, the term of this patent is extended or adjusted under 35 U.S.C. 154(b) by 2724 days.

(21) Appl. No.: 10/976,092

(22) Filed: Oct. 27, 2004

(65) Prior Publication Data

US 2006/0015169 A1    Jan. 19, 2006

Related U.S. Application Data

(60) Provisional application No. 60/588,847, filed on Jul. 15, 2004.

(51) Int. Cl.
*A61F 2/06* (2006.01)
(52) U.S. Cl. ........................................... 623/1.11
(58) Field of Classification Search .......... 604/507–510; 623/1.15–1.22
See application file for complete search history.

(56) References Cited

U.S. PATENT DOCUMENTS

| | | | |
|---|---|---|---|
| 5,709,224 A * | 1/1998 | Behl et al. ..................... 128/898 |
| 5,833,658 A | 11/1998 | Levy et al. |
| 6,090,136 A * | 7/2000 | McDonald et al. .......... 623/1.23 |
| 6,419,673 B1 * | 7/2002 | Edwards et al. ................. 606/41 |
| 6,485,500 B1 * | 11/2002 | Kokish et al. ................. 606/194 |
| 7,077,836 B2 * | 7/2006 | Lary et al. ..................... 604/509 |
| 2004/0254523 A1 * | 12/2004 | Fitzgerald et al. ............. 604/21 |
| 2005/0177103 A1 * | 8/2005 | Hunter et al. .............. 604/96.01 |
| 2008/0009902 A1 * | 1/2008 | Hunter et al. ................. 606/228 |

\* cited by examiner

*Primary Examiner* — Gary Jackson
*Assistant Examiner* — Eric Blatt

(57) ABSTRACT

Methods and apparatus for stabilizing vascular tissue adjacent the site of the placement of an intravascular repair vehicle such as a stent graft are provided. Thus, there is provided a method for stabilizing a segment of a blood vessel for placement of an intravascular repair vehicle comprising: isolating the segment of the blood vessel; infusing the isolated segment with a sclerosing agent creating a sclerosed segment; removing the sclerosing agent; and deploying the intravascular repair vehicle at the sclerosed segment.

8 Claims, 4 Drawing Sheets

METHODS FOR TREATMENT OF ANEURYSMAL TISSUE

RELATED APPLICATIONS

This application claims the benefit of U.S. Provisional Patent Application 60/588,847 filed Jul. 15, 2004.

FIELD OF THE INVENTION

The field of the invention is the treatment of vascular abnormalities.

BACKGROUND OF THE INVENTION

Aortic aneurysms pose a significant medical problem for the general population. Aneurysms within the aorta presently affect between two and seven percent of the general population and the rate of incidence appears to be increasing. This form of atherosclerotic vascular disease (hardening of the arteries) is characterized by degeneration in the arterial wall in which the wall weakens and balloons outward by thinning. Until the affected artery is removed or bypassed, a patient with an aortic aneurysm must live with the threat of aortic aneurysm rupture and death.

One clinical approach for patients with an aortic aneurysm is aneurysm repair by endovascular grafting. Endovascular grafting involves the transluminal placement of a prosthetic arterial stent graft within the lumen of the artery. To prevent rupture of the aneurysm, a stent graft of tubular construction is introduced into the aneurysmal blood vessel, typically from a remote location through a catheter introduced into a major blood vessel in the leg.

When inserted and deployed in a vessel, a stent graft acts as a prosthesis to maintain and restrict blood flow through the vessel. The stent graft typically has the form of an open-ended tubular element and most frequently is configured to enable its expansion from an outside diameter which is sufficiently small to allow the stent graft to traverse the vessel to reach a site where it is to be deployed, to an outside diameter sufficiently large to engage the inner lining of the vessel for retention at the site.

The customary procedure is to install a stent graft to bypass the aneurysmal site. The stent graft is expanded to engage the inner lining or inwardly-facing surface of the vessel wall with sufficient resilience to allow some contraction from full expansion size of the stent graft but also with sufficient stiffness so that the stent graft largely resists the natural recoil of the vessel wall—particularly at the ends of the stent graft where it encounters and creates a sealing engagement with healthy vessel tissue.

Despite the effectiveness of endovascular grafting, once the aneurysmal site is bypassed, the aneurysm remains. The aortic tissue can continue to degenerate such that the aneurysm increases in size due to thinning of the medial connective tissue architecture of the aorta and loss of elastin. Further, damage or advancement of the aneurysm to the neck area of the vessel where the stent graft makes contact with the vessel wall (beneath the renal arteries) can result in leakage and/or migration of the stent graft.

The use of sclerotherapy to treat large varicose veins was first attempted over 150 years ago, making it the oldest therapeutic technique in the treatment of varicose veins. Recent years have provided technology that has increased understanding of the anatomy and physiology of this process, enhancing its success in a wide range of situations and leading to application of sclerotherapy in other therapeutic techniques.

Thus there is a desire in the art to achieve a greater success of aneurysm repair including stabilization of the vessel adjacent the stent graft.

SUMMARY OF THE INVENTION

Embodiments according to the present invention address the problem of aneurysm repair, particularly the problem of continued breakdown of aneurysmal tissue and advancement of the aneurysm toward the region of the vessel adjacent to the renal arteries. Consequences of such continued breakdown include leakage of blood in to and rupture of the aneurysm or migration of the stent graft from its proper location in the vessel. Methods and apparatus for stabilizing the vessel tissue adjacent the aneurysmal site to prevent degeneration of the healthy vessel tissue are provided.

Thus, there is provided a method for stabilizing a segment of a blood vessel for placement of an intravascular repair vehicle comprising: isolating the segment of the blood vessel; infusing the isolated segment with a sclerosing agent creating a scierosed segment; removing the sclerosing agent; and deploying the intravascular repair vehicle at the sclerosed segment. Also provided is an apparatus for stabilizing a segment of a blood vessel for placement of a stent graft comprising: a dual balloon catheter; a delivery catheter; and a sclerosing agent.

BRIEF DESCRIPTION OF THE DRAWINGS

A more particular description of embodiments according to the present invention, briefly summarized above, may be had by reference to the present specification and the appended drawings.

FIG. 3A shows the balloons in a deflated state, and FIG. 3B shows the balloons in an inflated state.

DETAILED DESCRIPTION

Methods for stabilizing and treating an aneurysmal site include stabilizing the vessel tissue adjacent the aneurysmal site to prevent degeneration of healthy vessel tissue. Progression of the aneurysm and the concomitant degeneration of healthy tissue, particularly the neck region of the vessel, lead to the reduction in the length of the healthy vessel tissue with which the intravascular repair vehicle such as a stent graft may engage. This reduction may lead to loss of a tight juxtaposition or seal between the outer wall of the end of the stent graft and the inner wall of the vessel, causing leakage of blood into the aneurysmal sac and possible rupture of the aneurysm. In addition to or alternatively, loss of a tight juxtaposition between the outer wall of the end of the stent graft and the inner wall of the vessel may lead to migration of the stent graft resulting in blockage of, e.g., the renal arteries.

Figure 1:
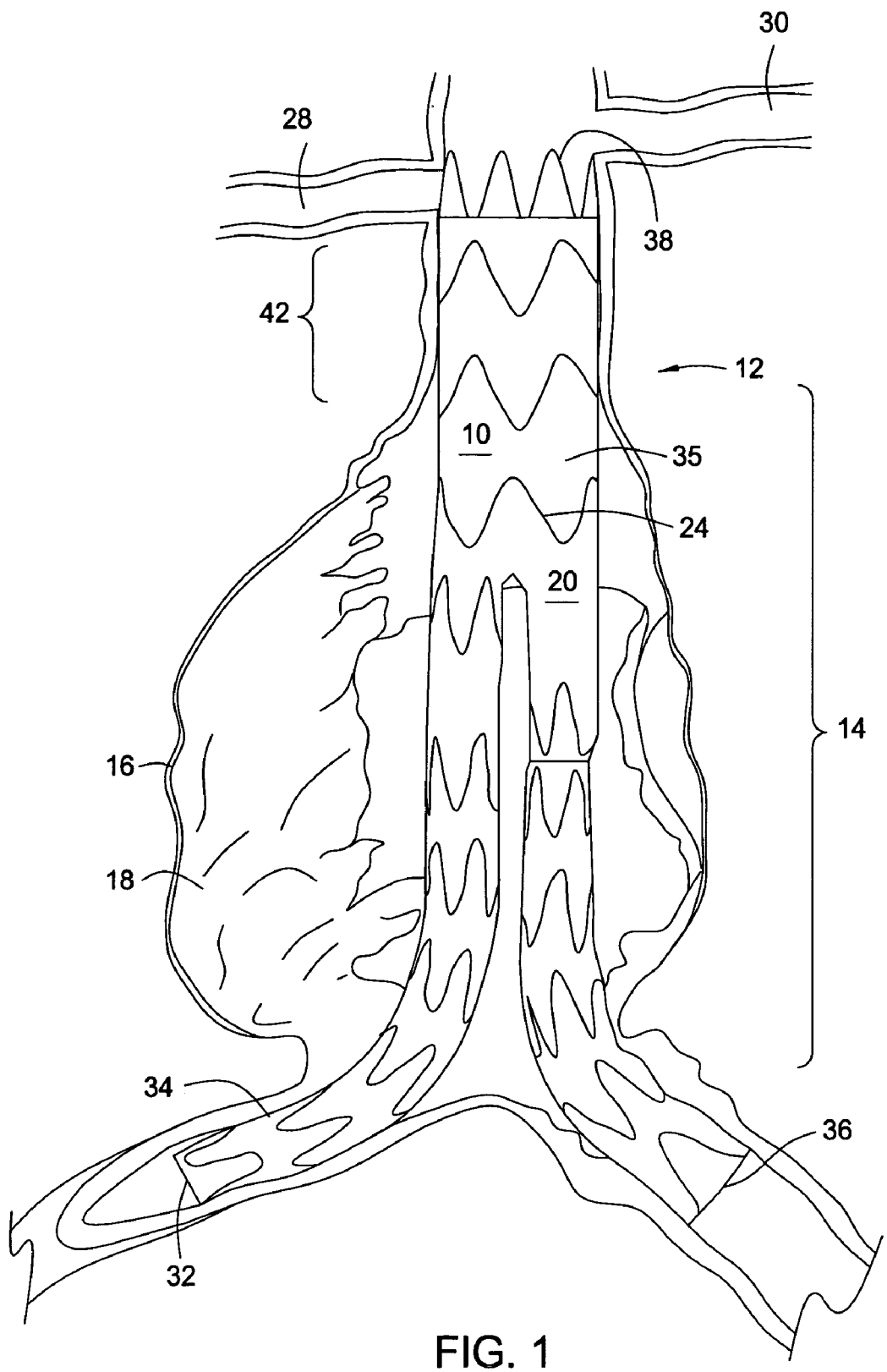
FIG. 1 is a partial sectional view of a descending aorta with a bifurcated stent graft placed therein.

Referring initially to FIG. 1, there is shown an intravascular repair vehicle, specifically a stent graft 10, positioned in a blood vessel, in this embodiment, an aorta 12, and spanning, within the aorta 12, an aneurysmal portion 14 of the aorta 12. The aneurysmal portion 14 is formed of a bulging of the aorta wall 16, in a location where the strength and resiliency of the aorta wall 16 is weakened. As a result, an aneurysmal sac 18 is formed of distended vessel wall tissue.

The stent graft 10 is positioned spanning the sac 18 and both provides a secure passageway for blood flow through the aorta 12 and seals off the aneurysmal portion 14 of the aorta 12 from contact with further blood flow through the aorta 12. The stent graft 10 includes a graft portion 20, which is configured from a biocompatible fabric, and which is sewn or otherwise attached to a stent structure (portion) which is configured, in this embodiment, as a plurality of sinusoidally shaped wires 24. The wires' stent springs are preferably made from a shape memory material, such as nitinol, which may be preset and heat treated to a predetermined diameter and shape. The superelastic properties of the wire are integrated with the stent graft which is compressed or rolled into a shape which will fit within a delivery tube such as a catheter. Once deployed from the catheter, the wires regain the shape they had when originally preset to hold the stent graft open.

The proximal or blood entry end 38 of the stent graft is positioned in the neck region of the vessel 42 below renal arteries 28 and 30, such that the renal arteries 28, 30 are not occluded. The distal or blood exit end 32 of the stent graft 10 is bifurcated into two branches 34, 36, each branch deployed to extend into and secure against the branch iliac arteries extending downstream from the aorta. The main body portion 35 of the stent graft 10 forms the proximal end. Branch 34 is integrally formed with body portion 35, and branch 36 is provided as a separate element which is combined, in situ in the patient, to form the bifurcated stent graft 10.

Blood flowing through the stent graft 10 is not continuous in pressure or flow, and in fact the pressure can fluctuate substantially, causing expansion and contraction of the stent graft, as well as axial (along the flow direction of the blood) forces on the stent graft 10. It has been found that these forces can be sufficient to disengage the stent graft ends from the blood vessel wall. The upper end of the stent graft may become compressed or crumpled, leading to stent graft/blood vessel seal failure at the entry (proximal) end 38 of the stent graft 10, and allowing fresh blood to enter the excluded aneurysmal sac 18, which may lead to aneurysm growth and eventual rupture.

Figure 2:
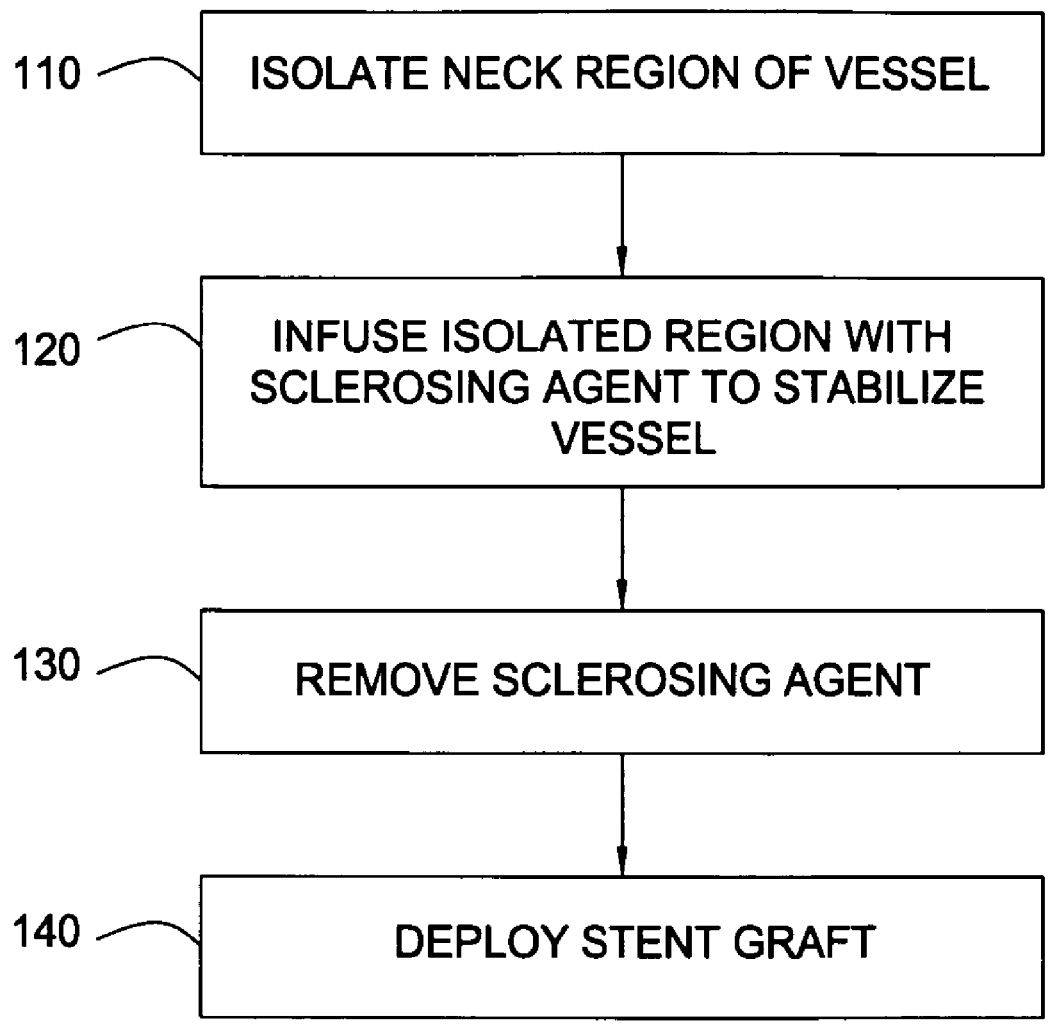
FIG. 2 is a flow diagram summarizing steps of one method according to the present invention.
Figure 3A:
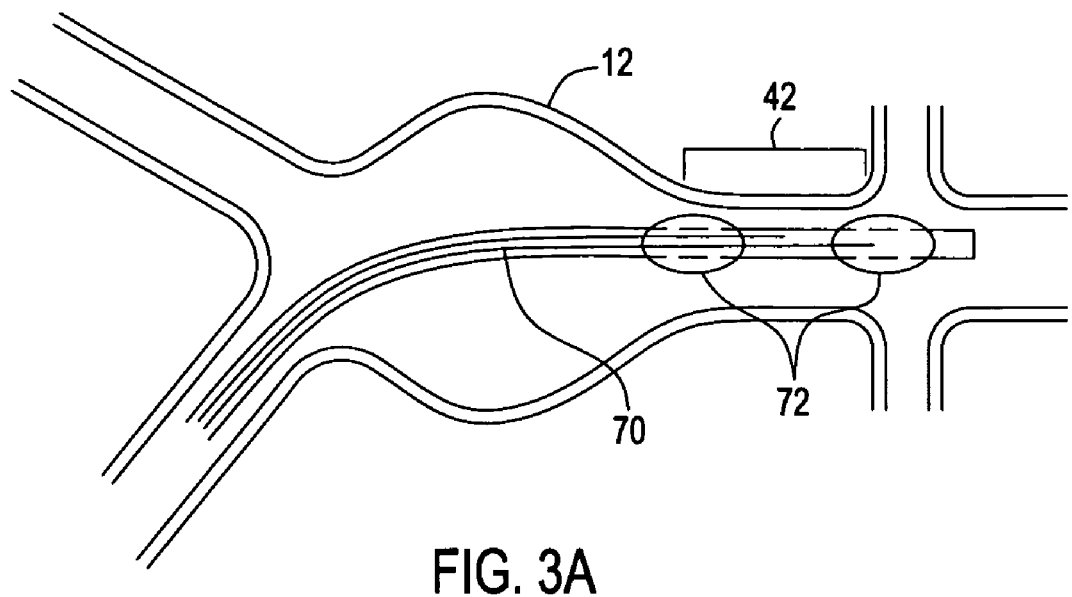
FIGS. 3A and 3B show a dual balloon catheter used for isolating a region in a vessel prior to infusion of a sclerosing agent.
Figure 3B:
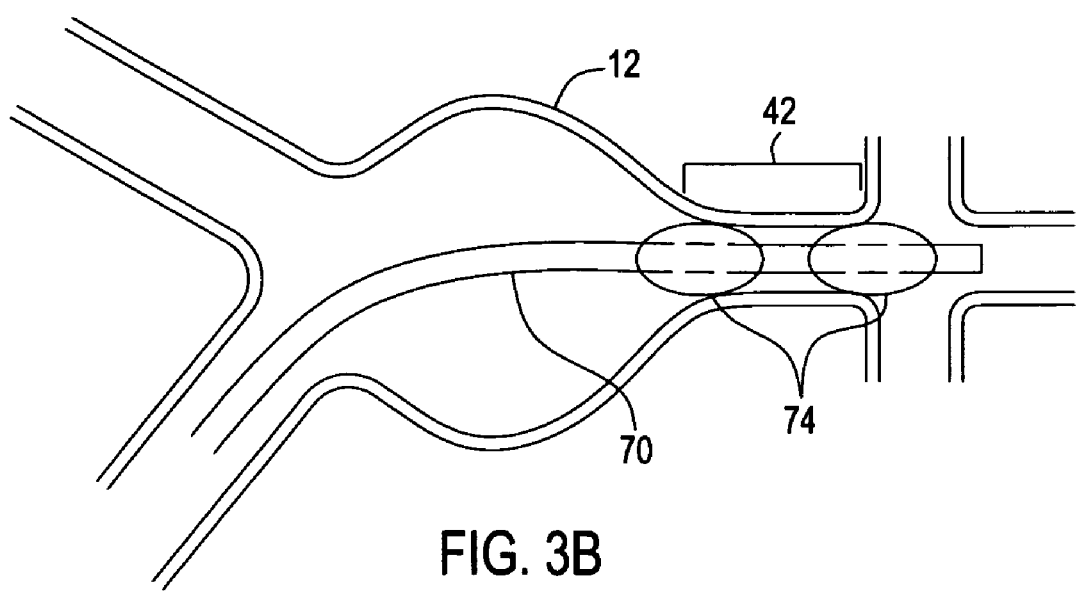

FIG. 2 is a flow chart summarizing the steps of the method according to one embodiment of the present invention. In step 110, the neck region (seen at 42 of FIG. 1) of an aorta is isolated. The isolation can be achieved by any method known in the art, such as by utilizing a dual balloon catheter. FIGS. 3A and 3B show the placement of a dual balloon catheter 70 in the neck region (from the lowest renal to the point where the diameter of the aorta begins widening at the top of the aneurismal sac) 42 of the aorta 12. The balloons of the catheter 70 are shown both in a deflated state 72 (FIG. 3A) and in an inflated state 74 (FIG. 3B). Thus, a dual balloon catheter having a pair of deflated, individually inflatable balloons is introduced into the neck region to be treated with a delivery means such as a delivery catheter positioned between the balloons. The two balloons are positioned so that they span the region to be treated. Once the balloons are in position, they are inflated so as to span the region.

At step 120, the isolated region of the vessel is infused with a sclerosing agent via a fluid lumen (or third and fourth lumens to provide separate entry and exit paths) in the delivery catheter to stabilize the vessel. In one embodiment, a dual balloon catheter is used. Such devices are known in the art; see, e.g., U.S. Pat. Nos. 4,404,971 and 4,520,823 to LeVeen et al., and U.S. Pat. No. 6,217,503 to Weinberger, et al. Essentially, one end of a dual lumen catheter with deflated balloons is introduced into the blood vessel. The end of the catheter with the deflated balloons is then advanced into the blood vessel to the area that is to be isolated, and positioned such that the two balloons are located on opposite sides of the area to be isolated. Fluid or gas is then introduced into the catheter and pressured to expand the balloons to a point that closes the blood vessel on each side of the area to be isolated. Next, the sclerosing agent is introduced through the second catheter and into the isolated area.

Vascular stabilization occurs only in response to irreversible endothelial cellular destruction and exposure of the underlying subendothelial cell layer to the sclerosing agent. It is important to use enough sclerosant to stabilize the vessel. If the introduced sclerosant is too weak, there may be no endothelial injury at all. However, if the introduced sclerosant is too strong, the vessel endothelium will be destroyed, but the sclerosant may also flow into and damage the outer vessel layers at the localized site, as well as affect adjacent normal vessel tissue that is not intended to be sclerosed. The key is to deliver a minimum concentration of sclerosant that will cause irreversible damage to the endothelium of the area of the vessel to be sclerosed, yet to protect the structural integrity of the outer layers of the vessel, while, in addition, leaving the adjacent normal vessel tissue intact. Once the agent has been delivered and has been allowed to sclerose the vessel, the sclerosing agent may be removed from the isolated area by draining from the second catheter, or the balloons can be deflated and the catheter apparatus withdrawn, in which case the blood reentering the isolated region of the vessel will dilute the scelorsing agent to a point where it is no longer active.

Figure 4:
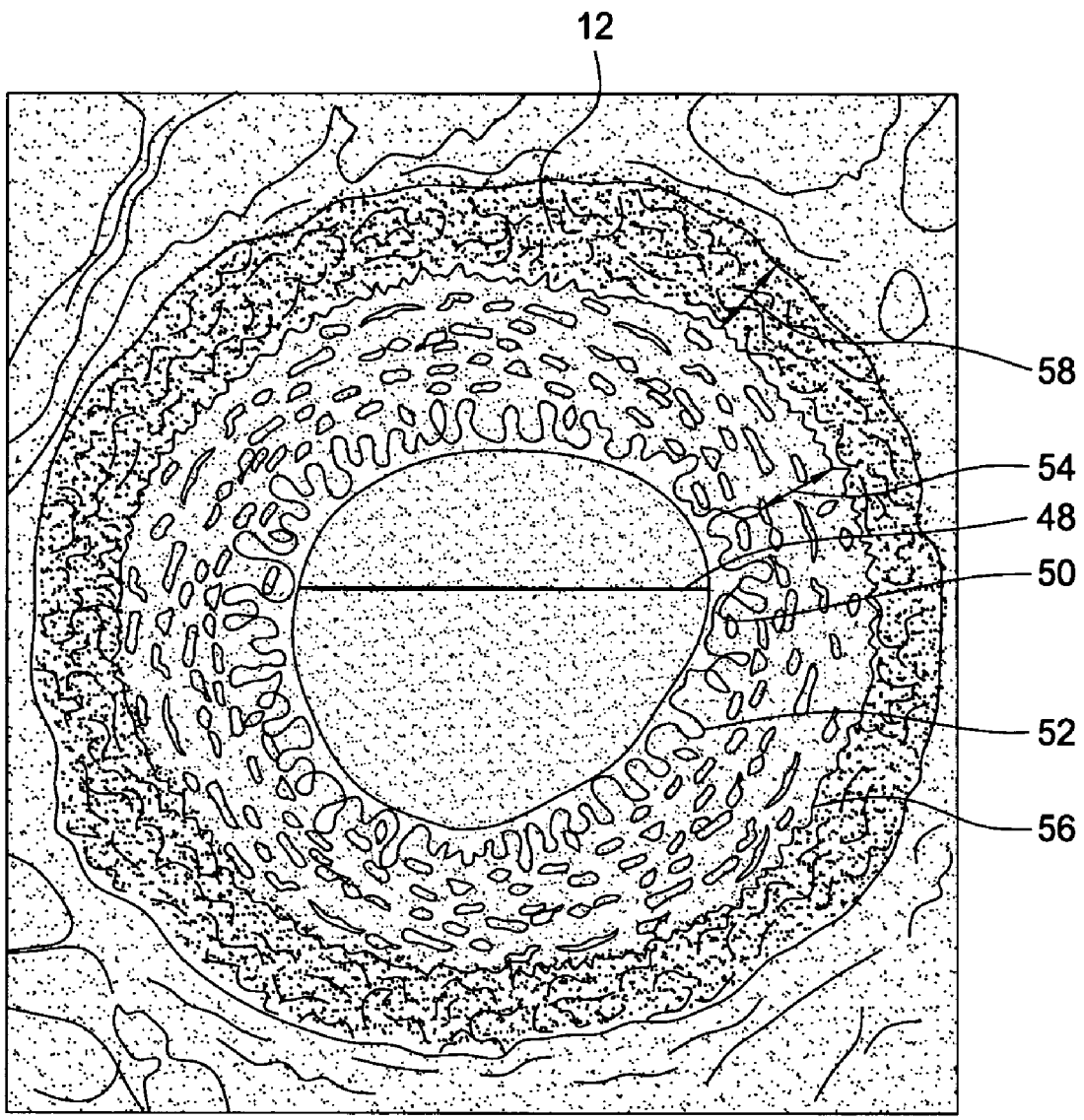
FIG. 4 is a graphic representation of a cross section of a blood vessel.

FIG. 4 shows a horizontal cross section of an artery. FIG. 4 shows an artery (e.g., aorta 12), having a tunica intima 50 surrounding on its inner surface, a lumen 48, and adjacent on its outer surface an internal or inner elastic lamina 52. Encircling the inner elastic lamina 52 is the tunica media 54. Adjacent the tunica media to the outside of the vessel is the outer or external elastic lamina 56, surrounded by the tunica adventitia 58.

The rational treatment of the neck of an aneurysmal aorta by chemical sclerosis depends upon the ability to produce endothelial damage—damage to the tunica media 50—that is irreversible in the localized area under treatment, but that does not extend to the outer vessel layers or to the adjacent vessel tissue, particularly the tunica media 54, the external elastic lamina 56 and the tunica adventitia 58.

As described, endothelial injury is limited to a controlled area by methods known in the art, such as by the use of dual balloon catheters. In addition, a thorough understanding of the mechanism of action of the sclerosing agent chosen is essential.

Virtually any foreign substance can be utilized to cause venous endothelial damage. Historical methods for producing venous endothelial trauma have included 'a slender rod of iron', reportedly used by Hippocrates himself, absolute alcohol, introduced by Monteggio and by Leroy D'Etoilles in the 1840s, and ferric chloride, introduced by Charles-Gabriel Pravaz in 1851. In 1910 it was noted that the injection of antisyphilitic mercurial drugs caused obliteration of antecubital veins, and these agents were adapted for use in sclerotherapy. There were many other drugs and techniques used for venous sclerosis during these years, but all of them suffered from one or another problem that made them unacceptable for modern use. Early sclerosing agents caused deaths from sepsis and from pulmonary embolism, as well as a high incidence of allergic reactions, local tissue necrosis, pain, and failed sclerosis.

In theory, the ideal sclerosant would have no systemic toxicity, be effective only above some threshold concentration so that its effects could be precisely localized through dilution, require a long period of contact to be effective so that dosage may be easily controlled, be non-allergenic, not cause staining or scarring, be perfectly soluble in normal saline, be painless upon injection, and, optimally, be inexpensive. However, no currently available sclerosant possesses all of the attributes of the perfect sclerosing agent. All currently available sclerosants fall short in one way or another, yet the variety of available agents is such that virtually every situation in which sclerotherapy is indicated can be safely and effectively handled by one or another of the available sclerosants, used alone or in combination.

In the 1930s, the class of drugs known as detergents, or as fatty acids and fatty alcohols, came into use in sclerotic therapy with the introduction of sodium morrhuate and sodium tetradecyl sulphate. Detergent sclerosants work by a mechanism known as protein theft denaturation, in which an aggregation of detergent molecules forms a lipid bilayer in the form of a sheet, a cylinder, or a micelle, which then disrupts the cell surface membrane and steals away essential proteins from the cell membrane surface.

The loss of these essential cell surface proteins causes a delayed cell death: when endothelial cell membranes are exposed to detergent micelles, scanning electron microscopy reveals irreversible cellular morphological changes occur within minutes, but the fatal cellular changes that are visible by normal light microscopy do not become apparent for many hours. Unlike many other agents, the detergent sclerosants do not cause hemolysis nor do they provoke direct intravascular coagulation.

At low concentrations, most detergent molecules are individually dissolved in solution, and there are very few micellar aggregates. When the concentration reaches some threshold (known as the critical micellar concentration, or CMC) nearly all further detergent molecules added to the solution will enter into micelles. Micelles can cause protein theft denaturation, but individual detergent molecules have no toxicity to the vascular endothelium. Thus, for each detergent sclerosant, there is some threshold concentration below which the agent causes no injury. This physical property means that detergent sclerosants offer significant benefits over many agents because they are potent agents that nonetheless have a clearcut threshold below which they have absolutely no injurious effect on vessel endothelium.

The solubility of detergents is inversely temperature dependent. Because of the highly polar nature of water and the entropic dependence of the hydrophobic effect, detergent molecules are much more soluble in cold solutions than in hot ones. This effect is easily seen in everyday life: dishwashing detergent produces a large amount of persistent foam in warm water, while cold water rinses away the soapy foam easily. The solubility of sclerosing agents such as polidocanol (described infra) is likewise much higher in cold solutions, and because single dissolved molecules are ineffective, the strength of the sclerosing effect is higher at warmer temperatures.

Detergent micellar formation can reach a maximum level based upon the temperature and upon the concentration of the detergent in solution. Micellar formation is a steric process, however, and the geometry of macroassemblies often prevents maximal micellar formation. The surface area of lipid bilayer structures such as sheets, cylinders and micelles is maximized when the solution is shaken to produce a foam. Because it is the surface of these structures that causes protein theft denaturation, a solution that has been shaken will be a more effective sclerosant than one that has not.

Sodium morrhuate is a detergent sclerosant made up of a mixture of saturated and unsaturated fatty acids extracted from cod liver oil. It was introduced in 1920s, and is still available today. Because it was in general use before there was any requirement to demonstrate safety or efficacy it has been exempted from the need for approval by the Food and Drug Administration (FDA) for sale in the United States, but there are several problems with the product that may make it a less than ideal agent for sclerotherapy. It is a biological extract rather than a synthetic preparation, and the composition varies somewhat from lot to lot. Its components have been incompletely characterized, and a significant fraction of its fatty acids and alcohols are of chain lengths that probably do not contribute to its effectiveness as a sclerosant. It is unstable in solution, causes extensive cutaneous necrosis if extravasated, and has been responsible for cases of anaphylaxis.

Ethanolamine oleate, a synthetic preparation of oleic acid and ethanolamine, has weak detergent properties because its attenuated hydrophobic chain lengths make it excessively soluble and decrease its ability to denature cell surface proteins. High concentrations of the drug are necessary for effective sclerosis. Allergic reactions are uncommon, but there have been reports of pneumonitis, pleural effusions, and other pulmonary symptoms following the injection of ethanolamine oleate into esophageal varices. Like sodium morrhuate, this agent was exempted from the need for approval by the Food and Drug Administration (FDA) for sale in the United States. The principal disadvantages of the drug are a high viscosity that makes delivery difficult, a tendency to cause red cell hemolysis and hemoglobinuria, the occasional production of renal failure at high doses (during varicose vein treatment), the possibility of pulmonary complications, and a relative lack of strength compared with other available sclerosants.

Sodium tetradecyl sulfate (Sodium 1-isobutyl-4-ethyloctyl sulfate) is a synthetic long chain fatty acid that has seen extensive industrial use as a synthetic surfactant (soap). It is sold for medical use as a solution of up to 3% concentration with 2% benzoyl alcohol used as a stabilant. It is effective as a sclerosing agent in concentrations from 0.1% to 3%. Like sodium morrhuate and ethanolamine oleate, it was 'grandfathered' by the Food and Drug Administration (FDA) for sale in the United States, but unlike sodium morrhuate, sotradecol has proven to be a reliable, safe and effective sclerosant. The principal clinical problems with the drug are a tendency to cause occasional cases of anaphylaxis, though with the localized treatment envisioned by the methods according to the present invention, the likelihood of anaphylaxis is remote.

Polidocanol (hydroxy-polyethoxy-dodecane) is a synthetic long-chain fatty alcohol sold under many trade names (Sclerovein, Aetoxysclerol, Aethoxysklerol, Etoxisclerol, Sotrauerix, Laureth 9). All commercially available formulations of polidocanol contain some small quantity of ethanol. The drug was originally developed and marketed in the 1950s under the name Sch 600 as a non-amide, non-ester local anesthetic that was useful for injected local anesthesia, as well as for epidural anesthesia and for topical mucosal anesthesia. It was first used as a sclerosing agent in Germany in the 1960s, and was quickly adopted for that use in most countries. The drug is not yet approved by the FDA for sale in the United States as a sclerosing agent, but is nonetheless widely used because it offers certain advantages over many other available drugs. As a local anesthetic, Polidocanol is painless upon injection. It does not produce necrosis if injected intradermally, and it has been reported to have a very low incidence of allergic reactions. The drug has been intensely studied and extremely well characterized, and has a high therapeutic index. The LD50 in rabbits is 200 mg/kg (approximately 5 times greater than that of Novocain), and the LD50 in mice is even greater, at 1200 mg/kg. For human use, the German manufacturer of polidocanol recommends a maximum daily dose of 2 mg per kg, although there have been reports of routine use with much higher doses. For all its advantages, polidocanol is not without problems as a sclerosant. Occasional anaphylactic reactions have been reported, though again, due to the localized delivery contemplated herein, the likelihood of anaphylaxis is remote.

Scleremo, a compound of 72% chromated glycerin, is a polyalcohol that often is considered a chemical irritant sclerosant. It is classified here with detergents because it is similar to the detergents in the way it causes cell surface protein denaturation. It is very popular in Europe, but it has not been approved by the FDA for use in the United States, where it is virtually unknown. Compared to other sclerosants it is a very weak sclerosant (it is approximately ¼ the strength of Polidocanol at the same concentration and volume) and has principally been used in the sclerosis of small varicose vessels. The main problems with scleremo are that it is hard to work with because it is extremely viscous, it can be quite painful on injection, the chromate moiety is highly allergenic, and it has occasionally been reported to cause ureteral colic and hematuria. Again, however, the methods according to the present invention involve localized application of the agent, and many side effects are substantially reduced if not eliminated.

Strong solutions of hypertonic saline and other salt solutions are part of a class of solutions that are often referred to as osmotic sclerosants. These solutions have long been regarded as causing endothelial death by osmotic cellular dehydration. Although it is true that osmotic dehydration at the point of injection is sufficient to rupture red blood cells and to dehydrate some nearby endothelial cells in varicose vein treatment, the evidence suggests that these sclerosants are effective even after dilution has reduced the osmotic gradient far too low to account for the effects seen. Thermodynamic and physical chemical calculations suggest that these and other strong ionic solutions probably work by causing conformational denaturation of cell membrane proteins in situ. Like the detergents, they can be diluted to the point where they have no further cellular toxicity.

Hypertonic solutions of saline became popular agents for sclerotherapy after they were adopted for that use by Linser in 1926. The most common preparations are a 20% or 23.4% solution. The principal advantage of hypertonic saline solutions is the fact that it is a naturally occurring bodily substance with no molecular toxicity. It has not been approved by the FDA for use in sclerotherapy, but it has been used successfully for that purpose by several generations of physicians. There are several reasons why it is not universally accepted as a desirable sclerosing agent in treating varicose veins. Because of dilutional effects, it is difficult to achieve adequate sclerosis of large vessels without exceeding a tolerable salt load. Further, it can cause significant pain on injection, and significant cramping after a treatment session. If extravasated, hypertonic saline solutions almost invariably cause significant necrosis. Because it causes immediate red blood cell hemolysis and rapidly disrupts vascular endothelial continuity, it is prone to cause marked hemosiderin staining that is not very cosmetically acceptable. Again, however, the methods according to the present invention do not result in dilution, and due to localized treatment, the side effects listed would be rendered moot. Thus, hypertonic saline soluctions are an option in the methods of the present invention.

Sclerodex is a mixture of 25% dextrose and 10% sodium chloride, with a small quantity of phenethyl alcohol. A primarily hypertonic agent, its effects are similar to those of pure hypertonic saline. It is not presently approved by the FDA for sale in the United States.

Polyiodinated iodine (Variglobin, Sclerodine) is a mixture of elemental iodine with sodium iodide, along with a small amount of benzyl alcohol. It is rapidly ionized and rapidly protein-bound when injected and most likely works by localized ionic disruption of cell surface proteins in situ. In vivo conversion of ionized iodine to iodide renders the solution ineffective as a sclerosant, thus localizing the sclerosing effects to the immediate area of delivery. The agent is not presently approved by the FDA for sale in the United States, but is widely used in Europe. The problems with this agent are the risks of anaphylaxis and of renal toxicity that are associated with ionic iodinated solutions.

Other chemical sclerosants exist that probably act by a direct or indirect chemical toxicity to endothelial cells: by poisoning some aspect of cellular activity that is necessary for endothelial cell survival. Such agents are less useful to the extent that they also poison other bodily cells. They also lack another of the key attributes of a good sclerosant: they remain toxic to some degree even after extreme dilution, so that there is no real threshold below which injury would not occur.

In the methods according to the present invention, one skilled in the art recognizes that the aim is to deliver the minimum concentration of the most appropriate sclerosant, and to inject it under conditions that will achieve the minimum effective exposure for the proper localized treatment of the vessel. Sclerosant concentration, volume, temperature, mixing, and patient positioning are more important in this endeavor than the choice of the actual sclerosing agent.

Once the sclerosing agent has been administered to stabilize the vessel (step 120), the sclerosing agent is removed (step 130) by the delivery catheter or by deflating the balloons and allowing the sclerosing agent to be diluted and dispersed into the bloodstream.

The result of steps 110, 120 and 130 should be a stabilized neck portion of the aneurysmal vessel. Once the vessel has been stabilized, a stent graft is deployed in a conventional manner to isolate the aneurysmal sac. Stent grafts of many types are known in the art.

Stent grafts normally are delivered into the lumen to be treated in a collapsed state with a diameter or crossing profile that is smaller than the diameter of the lumen. The stent grafts are then expanded with an expanding member, such as a balloon catheter, or are released from a constrained configuration and self-expanded by nature of their construction. The materials making up a stent portion may be a metal. Metal stents are known in the art, and metals such as stainless steel, nitinol (NiTi) and tantalum (Ta) have been used. In addition, various iron alloys have been used such as iron platinum, iron palladium, iron nickel cobalt titanium, iron nickel carbon, iron manganese silicon, and iron manganese silicon chromium nickel. Alternatively, the stent may comprise one or more biocompatible polymeric materials, preferably, non-degradable polymeric materials. In addition, one particularly preferred stent material is Inconel, a shape memory material. Generally the diameter of the metal or polymeric wire used for construction of the stent is between 0.005 inches to 0.02 inches.

The graft material may be any known in the art, and generally is an elastic material that can be expanded as the stent graft is expanded within the vessel. When the stent graft is constructed with a self-expanding stent, the graft material can be expanded with the expansion force inherent in the stent; alternatively, the stent graft can be expanded with a balloon catheter. Once a stent graft is expanded in the vessel, the stent graft will retain its expanded properties. In addition to its elastic nature, the graft material also is of a nature that, after expansion, it exhibits low residual stress to prevent wear and tear. Control of the elasticity of the graft material can control the necessary inflation pressure of the covered stent.

The thickness of the graft material optionally is minimized to reduce the over all cross sectional thickness of the stent graft and the pressure necessary to deploy it. Generally, the graft material will be thinner than 0.005 inch, and may be thinner than 0.002 inch. The thickness of the graft material can be consistent over the length of the stent or the thickness can vary. For example, the graft material can be thinner adjacent the ends and thicker in the middle. A thinner graft material at the ends of the stent graft may reduce the leading cross section of the stent graft when it is introduced into the vessel. Also, the thickness of the graft material may vary along the length of the stent graft to control the inflation characteristics of the stent graft. For example, it may be advantageous for the stent to inflate or expand in the middle first. Varying thickness of the cover would vary the inflation pressure necessary to deploy the stent in various portions and thereby control inflation characteristics.

All references cited herein are to aid in the understanding of the invention, and are incorporated in their entireties for all purposes.

What is claimed is:

1. A method for stabilizing a segment of a blood vessel for placement of an intravascular repair vehicle comprising:
    isolating the segment of the blood vessel;
    infusing the isolated segment with a sclerosing agent creating a sclerosed segment;
    removing the sclerosing agent; and
    deploying the intravascular repair vehicle at the sclerosed segment.

2. The method of claim 1, wherein the isolating step is achieved by use of a dual balloon catheter.

3. The method of claim 1, wherein the infusing step is performed by a delivery catheter.

4. The method of claim 1, wherein the intravascular repair vehicle is a stent or stent graft.

5. The method of claim 1, wherein the removing step is performed by a delivery catheter.

6. The method of claim 1, wherein the sclerosing agent is sodium morrhuate, ethanolamine oleate, sodium tetradecyl sulfate, polidocanol, scleremo, hypertonic saline solution, sclerodex, or polyiodinated iodine.

7. A method for stabilizing a segment of a blood vessel for placement of a stent graft comprising:
    isolating the segment of the blood vessel by deployment of a dual balloon catheter;
    infusing the isolated segment with a sclerosing agent using a delivery catheter creating a sclerosed segment;
    using the delivery catheter to remove the sclerosing agent; and
    deploying the stent graft at the sclerosed segment.

8. The method of claim 7, wherein the sclerosing agent is sodium morrhuate, ethanolamine oleate, sodium tetradecyl sulfate, polidocanol, scleremo, hypertonic saline solution, sclerodex, or polyiodinated iodine.

* * * * *